(12) United States Patent
El-Habbal

(10) Patent No.: US 10,045,984 B2
(45) Date of Patent: Aug. 14, 2018

(54) COMBINATION THERAPY

(76) Inventor: Magdi El-Habbal, North Ferriby (GB)

( * ) Notice: Subject to any disclaimer, the term of this patent is extended or adjusted under 35 U.S.C. 154(b) by 1011 days.

(21) Appl. No.: 12/920,345

(22) PCT Filed: Feb. 27, 2009

(86) PCT No.: PCT/EP2009/052394
§ 371 (c)(1),
(2), (4) Date: Aug. 31, 2010

(87) PCT Pub. No.: WO2009/109531
PCT Pub. Date: Sep. 11, 2009

(65) Prior Publication Data
US 2011/0045070 A1 Feb. 24, 2011

(30) Foreign Application Priority Data

Mar. 3, 2008 (GB) .................................. 0803948.9

(51) Int. Cl.
*A61K 31/505* (2006.01)
*A61K 33/30* (2006.01)

(52) U.S. Cl.
CPC ............ *A61K 31/505* (2013.01); *A61K 33/30* (2013.01)

(58) Field of Classification Search
None
See application file for complete search history.

(56) References Cited

U.S. PATENT DOCUMENTS 5,637,311 A * 6/1997 Pallenberg .................... 424/434

OTHER PUBLICATIONS

Iqbal, M.S.; Khan, A. H.; Loothar, B. A.; Bukhari, I. H. Effect of derivatization of sulfamethoxazole and trimethoprim with copper and zinc on their medicinal value. Med. Chem. Res. 2009, 18, pp. 31-42.*
Simo, B.; Perello, L.; Ortiz, R.; Castineiras, A.; Latorre, J.; Canton, E. Interactions of metal ions with a 2,4-diaminopyrimidine derivative (trimethoprim) Antibacterial studies. Journal of Inorganic Biochemistry, 81 (2000), 275-283.*
Roxas, Mario; Jurenka, Julie. Colds and Influenza: A review of diagnosis and conventional, botanical, and nutritional considerations. Alternative Medicine Review, vol. 12, No. 1, 2007.*
http://www.thefreedictionary.com/pill as referenced on May 20, 2013.*
Rehmani, Fouzia S., et al., "Coordination of septran drug with trace metal ions in the biological system," International Journal of Biology and Biotechnology, Apr. 2006, pp. 439-442, vol. 3, No. 2.
Flore, O., et al., "Inhibitory action of 2,4 diamino 5 (3, 4, 5 trimethoxybenzyl) pyrimidine (trimethoprim) on the growth of DNA viruses," Rivista di Farmacologia e Terapia, 1974, pp. 201-204, vol. 5, No. 3.
Goldberg, S. et al., "Inhibition of herpesvirus replication by trimethoprim and cotrimoxazole," Clinical Research, p. 676A, vol. 24, No. 5.
Turner, R.B., et al., "Effect of Treatment with Zinc Gluconate or Zinc Acetate on Experimental and Natural Colds," Clinical Infectious Diseases, Nov. 1, 2000, pp. 1202-1208, vol. 31, No. 5, The University of Chicagl Press, Chicago, IL.

* cited by examiner

*Primary Examiner* — Jessica Worsham
(74) *Attorney, Agent, or Firm* — Posternak Blankstein & Lund LLP

(57) ABSTRACT

The present invention provides a composition comprising zinc and trimethoprim, particularly in a weight ration of about 1:3 to about 1:7, as well as a sustained- or prolonged-release preparation which comprises trimethoprim and zinc and a biodegradable polymer providing a clinically useful composition which has prolonged release over a long period of time.

9 Claims, 8 Drawing Sheets

COMBINATION THERAPY

CROSS REFERENCE TO RELATED APPLICATION

This application is for entry into the U.S. National Phase under § 371 for International Application No. PCT/EP2009/052394 having an international filing date of Feb. 27, 2009, and from which priority is claimed under all applicable sections of Title 35 of the United States Code including, but not limited to, Sections 120, 363 and 365(c), and which in turn claims priority under 35 USC 119 to U.K. Patent Application No. 0803948.9 filed on Mar. 3, 2008.

BACKGROUND OF THE INVENTION

Virus infection of the upper air way is perhaps the most common infection in human. A variety of agents are associated with acute viral respiratory tract infections (VRTI) including picornavirus (rhinovirus, most commonly), coronavirus, respiratory syncytial virus (RSV), influenza A and B, parainfluenza viruses, and adenovirus. The clinical syndromes of acute VRTI range from mild illnesses such as the common cold to severe, potentially life-threatening conditions such as severe influenza A infection.

The importance of VRTI is immense. There are considerable costs associated with VRTI in terms of decreased productivity and time lost from work or school, visits to healthcare providers, and amount of drugs prescribed. Recent data suggest that the total annual cost of VRTIs in the United States is $25 billion [Fendrick A M, et al., Value in Health 2001; 4:412]. Approximately 500 million episodes of VRTI occur each year in the US accounting for 84 million visits to clinicians [ibid.]. Another important factor contributing to the impact of VRTIs is the inappropriate use of antibiotics. This significantly adds to the cost of management and to the increasing prevalence of antibiotic-resistant bacteria.

Moreover, the possible effects of the next influenza pandemic has been estimated in the United States to result in 89,000 to 207,000 deaths, 314,000 to 734,000 hospitalizations, 18 to 42 million outpatient visits, and 20 to 47 million additional illnesses (Fendrick A M, 2001). Patients at high risk (15% of the population) would account for approximately 84% of all deaths. The estimated economic impact is US$71.3 to $166.5 billion, excluding disruptions to commerce and society (Meltzer M I, et al., Emerging Infectious Diseases 5: 659-671; 1999).

At present, vaccination is applied to prevent such pandemics and make cost savings. An intake of 60% is needed to be economically viable. That is not easily achieved and may not be possible within the time required for vaccine effectiveness, especially if two doses of vaccine are required.

Thus, there is a need for a treatment that is effective when viral disease strikes, that is easily administered, is rapidly acting and terminates the illness in a short time.

DESCRIPTION OF THE RELATED ART

Zinc has been used to treat the common cold (Turner R B, et al., Clin Infect Dis 2000, 31: 1202-1208). Zinc affects viral replication when present in a subject in a concentration of 0.05 mMolar, but is believed to be effective if given only within 24 hours of the start of the illness (George A. Eby. Handbook for Curing the Common Cold, George Eby Research, Austin, Tex. USA, 1994, 9-24).

Trimethoprim is a potent metabolic inhibitor of bacterial dihydrofolic acid reductase and a highly active antibacterial agent against strains resistant to other antibiotics frequently used such as β-lactam antibiotics (M. Fresta, et al., Antimicrob. Agents Chemother. 40 (12) 1996, 2865). Trimethoprim is a pyrimidine derivative that competitively inhibits the production of dihydrofolate reductase that blocks thymidine synthesis, essential for DNA formation, and in effect causes alteration in cell membrane. Thus, trimethoprim is a candidate for impairing viral binding to cell wall for endocytosis. Pyrimidine and pyrimidinyl derivatives are thought to inhibit viral transmission (E De Clercq, Nature Reviews, December 2006, Vol 5, 1015-1025).

Trimethoprim metal complexes with copper, cadmium and zinc metal ions have been reported to show antibacterial activity (B. Simó et al., Journal of Inorganic Biochemistry, 81 (2000), 275-283). Antibacterial preparations comprising a large number of agents including among others trimethoprim have been proposed (see for example, U.S. Pat. Nos. 6,911,525 and 6,518,252, U.S. Patent Application Publication Nos. 2004/0071757 and 20040071757), but none specifically discloses a trimethoprim-zinc combination.

Respiratory viruses are RNA viruses that replicate in the ribosomes where amino acids are presented for the replication process. Inhibition of such delivery would result in hampering viral replication. Disturbing DNA function in a subclinical way would have an impact on the virus but not on the human cell. Such an approach would prevent viral replication and would overcome the potential development of mutant strains that can be more difficult to treat (see E De Clercq, 2006, reporting that such a combined therapy may be needed with its potential side effects and costs).

To date, no such combined therapy has been reported.

A simply administered, readily and cheaply available treatment for a viral infection, particularly a respiratory viral infection that brings about full, or even partial, recovery within a short space of time would be invaluable, not just for bringing the patient back to health, but also to prevent the increased likelihood of opportunistic infections.

SUMMARY OF THE INVENTION

Therefore, in a first aspect of the invention is provided an antiviral composition comprising zinc and trimethoprim.

It has been surprisingly found that an antiviral composition comprising zinc and trimethoprim is highly effective in treating both moderate and severe viral infection of the respiratory tract, reducing morbidity and mortality, and shown to be effective when administered at any time during the disease process, shortening the duration of illness. This zinc and trimethoprim combination shows promise for the preventing of pandemic influenza infections and its devastating consequences, and reducing the economic burden of epidemics.

In one embodiment, the composition comprises an admixture of zinc and trimethoprim.

The inventive zinc and trimethoprim compositions are found to be surprisingly effective against several different types of viral infection, for example, an acute viral respiratory tract infection including a picornavirus such as a rhinovirus, a coronavirus, respiratory syncytial virus, an influenza virus, such as for example, influenza A and B, a parainfluenza virus, adenovirus, or a viral infection of one or more of the heart, the muscles, the liver and the skin. It will be evident to those skilled in the art that there are several in vivo target sites of activity. For example, in addition to upper or lower respiratory system the air ways and lungs, the inventive approach may also be applied to viral infections of other organs such as the heart, the muscles, liver and skin. The inventive composition is found to be effective in bringing about an end to influenza and its subtypes and/or in shortening the duration of illness.

Preferably the subject is a human or animal mammalian, more preferably human. The composition has an antiviral effect in a subject in vivo.

In one embodiment, a composition is provided comprising zinc and trimethoprim, wherein the weight ratio of zinc to trimethoprim is from about 1:3 to about 1:7.

In another embodiment, the composition comprises between about 0.1 and 200 mg zinc and between about 50 mg and about 1000 mg trimethoprim.

The composition may comprise different amounts of zinc and trimethoprim, depending upon the clinical indication and the amount of the composition to be administered to the subject in need, whilst maintaining the weight ratio of zinc and trimethoprim of between about 1:3 and about 1:7.

For example, the composition of zinc and trimethoprim may comprise a weight ratio of about 0.1-5 mg zinc:about 0.5-28 mg trimethoprim, or 18 mg zinc:82 mg trimethoprim, or 72 mg zinc:328 mg trimethoprim, or 150 mg zinc:650 mg trimethoprim, or 0.18 mg zinc:1 mg trimethoprim, or from about 16-200 mg zinc:about 50-1000 mg trimethoprim, or about 0.1-200 mg zinc:about 50-1000 mg trimethoprim.

For example, the composition of zinc and trimethoprim may comprise about 0.1-5 mg zinc and about 0.5-28 mg trimethoprim, or 18 mg zinc and 82 mg trimethoprim, or 72 mg zinc and 328 mg trimethoprim, or 150 mg zinc and 650 mg trimethoprim, or 0.18 mg zinc and 1 mg trimethoprim, or from about 16-200 mg zinc and about 50-1000 mg trimethoprim, or about 0.1-200 mg zinc and about 50-1000 mg trimethoprim.

For example, zinc in amounts of between 0.1 mg, 0.5 mg, 1 mg, 5 mg, 22.5 mg, 50 mg, 100 mg, 150 mg and 250 mg, and trimethoprim in amounts of between 1 mg, 5 mg, 10 mg, 25 mg, 80 mg, 160 mg, 100 mg, 200 mg, 500 mg and 1000 mg, may be administered to a subject twice daily for 2 to 5 days. The zinc/trimethoprim concentration ratios above may be varied to suit all ages (neonates, children, adults and elderly), including an immune compromised subject.

In a further embodiment, the composition may further comprise one or more of: an adjuvant, a buffer, an excipient, a carrier, a matrix, a binder, a coating material, an analgesic, a vitamin, a sweetener a flavour, a prolonged release vehicle and an additional therapeutic agent.

The composition may be administered to the subject either orally or by injection, and may be combined with any one or combination of: a drug-releasing polymer, matrix, bead, microcapsule, or other solid drug-releasing vehicle; drug-releasing tiny timed-release pills or mini-tablets; compressed solid drug delivery vehicle; controlled release binder; multi-layer tablet or other multi-layer or multi-component dosage form. It will be evident to those skilled in the art that oral administration of the antiviral composition may optionally be via an enterically coated form.

The composition may also further comprise one or more therapeutic agents active against the same disease state. When the inventive composition is used in combination with a second therapeutic agent active against the same disease state, they may conveniently be administered alone or in combination, in either single or multiple doses, sequentially or simultaneously, by the same route of administration, or by a different route.

Tablets may contain the active ingredient in admixture with non-toxic pharmaceutically-acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example corn starch or alginic acid; binding agents, for example, starch, gelatin or acacia; and lubricating agents, for example magnesium stearate, stearic acid or talc.

The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in U.S. Pat. Nos. 4,356,108; 4,166,452; and 4,265,874, incorporated herein by reference, to form osmotic therapeutic tablets for controlled release.

Formulations for oral use may also be presented as hard gelatine capsules where the active ingredient is mixed with an inert solid diluent, for example, calcium carbonate, calcium phosphate or kaolin, or as soft gelatine capsules wherein the active ingredient is mixed with water or an oil medium, for example peanut oil, liquid paraffin, or olive oil.

The composition may be formulated as an injectable fluid, a prolonged release medication, an aerosol, an aerosol, a gel, a pill, a capsule, a lozenge, a gargle, a nasal drop, an eye drop, a syrup, a dissolvable tablet, an enterically coated tablet, a dermal application or a transdermal patch.

Administration of the zinc/trimethoprim admixture compositions according to the invention may be through several routes of administration, for example, oral, rectal, nasal, pulmonary, topical (including buccal and sublingual) or dermal, transdermal, intracisternal, intraperitoneal, vaginal and parenteral (including subcutaneous, intramuscular, intrathecal, intravenous and intradermal) route. It will be appreciated that the preferred route will depend on the general condition and age of the subject to be treated, the nature of the condition to be treated and the active ingredient chosen.

For topical use, sprays, creams, ointments, jellies, gels, inhalants, dermal patches, implants, solutions of suspensions, etc., containing the compounds of the present invention are contemplated. For the purpose of this application, topical applications shall include mouth washes and gargles.

The composition may comprise a pharmaceutically acceptable salt of any one or more of: zinc, trimethoprim, and an admixture of zinc and trimethoprim.

Pharmaceutically acceptable salts of the zinc and trimethoprim composition may include enantiomers, polymorphs, solvates, hydrates, and combinations thereof. Prodrugs of either zinc or trimethoprim are also contemplated.

The invention also covers derivatives based on zinc and trimethoprim admixtures.

In the inventive compositions, the term "pharmaceutically acceptable salt" is intended to indicate salts which are not harmful to the patient. Such salts include pharmaceutically acceptable acid addition salts, pharmaceutically acceptable metal salts, ammonium and alkylated ammonium salts, salts of inorganic acids and of organic acids. Further examples of pharmaceutically acceptable inorganic or organic acid addition salts include the pharmaceutically acceptable salts listed in J. Pharm. Sci. 1977, 66, 2.

The zinc/trimethoprim admixture compositions according to the invention may be formulated with pharmaceutically acceptable carriers or diluents as well as any other known adjuvants and excipients in accordance with conventional techniques such as those disclosed in Remington: The Science and Practice of Pharmacy, 19$^{th}$ Edition, Gennaro, Ed., Mack Publishing Co., Easton, Pa., 1995.

The composition may further comprise a buffer system, preservative(s), tonicity agent(s), chelating agent(s), stabilizers and surfactants, which is well known to the skilled person. For convenience reference is made to Remington: The Science and Practice of Pharmacy, 20th edition, 2000.

According to the inventive approach, the zinc and trimethoprim may be combined in vitro and administered to the subject thereafter. The inventive compositions may be prepared by mixing zinc and trimethoprim to provide an admixture prior to administration to a subject in need. The zinc and trimethoprim may be micronized either before combining or after combining together. Alternatively, the zinc and trimethoprim may be administered separately and sequentially to the subject at any point during treatment (such as the one being administered followed by the other being administered).

The invention also covers zinc and trimethoprim complexes.

Equally and alternatively, the inventive compositions may comprise a complex of zinc and trimethoprim in which the complex may be a complex salt formed by various kinds of intermolecular bonding between zinc and trimethoprim.

For example, a complex of zinc and trimethoprim in the present invention is produced by mixing trimethoprim and a water-soluble zinc salt in a weight ratio of about 1:3 to about 1:7, in a aqueous solvent, such as for example water or aqueous solutions containing ethanol at about 1 to about 10% w/w, which does not exert an adverse influence on the solubility of trimethoprim and a water-soluble zinc salt, allowing from 1 minute to 1 hour at a temperature ranging from 4° C. to 37° C.

The complex may be a compound (complex salt, double salt, salt, and organic metal compound etc.) formed by intermolecular binding between zinc and trimethoprim or a mixture of the two in which other forms of association exist. Trimethoprim and/or zinc which do not form a complex may be present.

The pH of an aqueous solution resulting from the present compositions may be controlled such that the bioactivity of trimethoprim and zinc is not affected, and may be adjusted to be weakly acidic, neutral, or weakly alkaline pH.

The zinc salt may be one or more of: $C_{14}H_{18}N_4O_3 \cdot ZnSO_4$, $C_{14}H_{18}N_4O_3 \cdot ZnO_{14}H_{22}C_{12}$, and $C_{14}H_{18}N_4O_3 \cdot ZnC_4H_6O_4$, or a derivative thereof.

The zinc salt may comprise one or more of: zinc sulphate, zinc acetate and zinc gluconate.

Water-soluble zinc salts may include salts of zinc and inorganic acids, salts of zinc and organic acids. Inorganic acids may for example include hydrochloric acid, sulphuric acid, or nitric acid. Organic acids may for example include aliphatic carboxylic acids, or aromatic acids.

The composition may comprise one or more of Structures 1-14 as shown below, or a derivative thereof.

The Structures 1 to 14 listed in Table 1 below show alternative stereochemical representations of how the zinc and trimethoprim may be combined in the one or more zinc/trimethoprim composition of the present invention. The compounds may thus be in stable non-interacting and/or interacting states. Zinc can be present in the composition associated with different positions of the trimethoprim molecule or be bonded to the side chains in any combination with and without being present in the folded molecule, as well as in the free state between two or more molecules of the trimethoprim compound, such as is exemplified in Table 1 below.

In a second aspect of the invention is provided an antiviral composition comprising zinc and trimethoprim for use in treating a viral infection in a subject.

In a third aspect of the invention is provided a use of an antiviral composition comprising zinc and trimethoprim for the manufacture of a medicament for treatment of a viral infection in a subject.

The composition may be administered to the subject once, twice, three times or four times a day. It will be evident that the individual choice of dosage and frequency of administration will be based on age and severity of disease and determination of the ideal dosage may have recourse to the clinical indicia, as will be within the understanding of those skilled in the art.

The inventive approach also contemplates the inclusion in a zinc and trimethoprim composition of a prolonged release component. The compositions and uses of the invention may also employ therapeutically effective dosage amounts of zinc and trimethoprim, formulated in a sustained or prolonged release composition or dosage form. A prolonged release component would be particularly effective if combined with pain relief.

A sustained release complex of the zinc and trimethoprim may be made, therefore, by dispersing a powder of the zinc and trimethoprim complex combined in a weight ratio of about 1:3 to about 1:7, into a solution of a biodegradable polymer according to methods well known to those skilled in the art. Such a sustained release preparation may be usefully prepared as an aqueous suspension suitable for injection using one of the commonly employed dispersing agents, such as Tween 80® for example. Alternatively, a sustained release complex may be prepared for use as oral capsules, granules, powders, liquid suspensions and the like.

The active composition may be released from the sustained release compositions and delivered into the stomach, the intestinal lumen, the blood or other target site of activity in the subject at a sustained therapeutic level over a period of at least about 6 hours, or over a period of at least about 8 hours, at least about 12 hours, or at least about 18 hours, or over a period of about 24 hours or greater. The compositions whether immediately released or as sustained release compositions will yield a therapeutic level of the zinc/trimethoprim composition following administration to a subject in a desired dosage amount, e.g. 0.1 mg, 0.5 mg, 1 mg, 5 mg, 22.5 mg, 50 mg, 100 mg, 150 mg or 250 mg of zinc and 1 mg, 5 mg, 10 mg, 25 mg, 80 mg, 160 mg, 100 mg, 200 mg, 500 mg or 1000 mg of trimethoprim over a period of at least about 6 hours, at least about 8 hours, at least about 12 hours, at least about 18 hours, or up to 24 hours or longer.

In a sustained release composition according to the invention, from 0% to 20% of the active composition is released and delivered within in 0 to 2 hours, from 20% to 50% of the active compound is released and delivered within about 2 to 12 hours, from 50% to 85% of the active compound is released and delivered within about 3 to 20 hours, and greater than 75% of the active compound is released and delivered within about 5 to 18 hours.

The trimethoprim and zinc is substantially water-soluble and may be easily micronised without lowering the activity of the trimethoprim and zinc combination. If the trimethoprim and zinc combination is micronized to a small particle diameter, the prolonged-release preparation can be produced on a large scale with assured stability and without denaturalizing trimethoprim in the process, having also an enhanced entrapment of the trimethoprim and zinc and an improvement in release properties.

Methods to produce controlled release systems useful for compositions of the current invention include, but are not limited to, crystallization, condensation, micronisation, co-crystallization, precipitation, co-precipitation, emulsification, dispersion, high pressure homogenisation, en-capsulation, spray drying, microencapsulating, coacervation, phase separation, solvent evaporation to produce microspheres, extrusion and supercritical fluid processes. General reference is made to Handbook of Pharmaceutical Controlled Release (Wise, D. L., ed. Marcel Dekker, New York, 2000) and Drug and the Pharmaceutical Sciences vol. 99: Protein Composition and Delivery (MacNally, E. J., ed. Marcel Dekker, New York, 2000).

A powdered form of the trimethoprim and zinc composition is useful for producing a sustained-release preparation on a large scale. For example, a complex of trimethoprim and zinc can be obtained as a powder with a mean particle diameter of less than about 10 μM.

Where the complex is dispersed into an organic solvent containing a biodegradable polymer, particles having a small diameter are very useful for obtaining an acceptable entrapment ratio of the complex and a prolonged release. For example, an entrapment ratio of the complex in the sustained-release preparation is preferably more than about 90% with an initial burst ratio of the trimethoprim and zinc preferably less than about 50%. The content of the trimethoprim and zinc composition in a sustained-release preparation of the present invention may be about 0.1% (w/w) to about 40% (w/w).

The biodegradable polymer may be a high-molecular polymers being slightly soluble or insoluble in water, such as aliphatic polyesters (e.g., homopolymers, copolymers or mixtures thereof), hydroxydicarboxylic acids hydroxytricarboxylic acids, poly-α-cyano acrylic acid esters, polyamino acids such as poly-.gamma.-benzyl-L-glutamic acid. The type of polymerization may be random, block or graft.

In a fourth aspect of the invention is provided a method of treatment for a subject in need at any time during a viral infection, wherein zinc and trimethoprim are administered to the subject. The treatment may comprise either simultaneous administration of an admixture of zinc or trimethoprim, or sequential administration of zinc and trimethoprim in either order, or may comprise administering a zinc and trimethoprim complex to the subject. Specifically, the invention provides a method of treatment of a viral respiratory infection in a subject, or a viral infection of the respiratory system, upper or lower. The method of treatment may further comprise administering zinc and trimethoprim for an acute viral respiratory tract infection including for example a picornavirus, such as rhinovirus, a coronavirus, respiratory syncytial virus, influenza A and B, parainfluenza viruses and adenovirus.

In a fifth aspect of the invention, a kit is provided comprising: i) an antiviral composition as described herein; ii) one or more of a hydrophobic organic carrier, an organic polar solvent, an emollient, a surface-active agent; at least one polymeric additive selected from a delayed release agent, bioadhesive agent, a gelling agent, a film forming agent, a phase change agent, water and mixtures thereof; and optionally, instructions for use.

The inventive approach thus provides a therapeutic kit to provide an effective dosage of an antiviral agent. The kit would be applicable in a variety of different clinical and lay settings for treating viral infections of different organs such as lung, air ways, heart, liver, muscles, skin (e.g. a herpes infection). The kit could also be added to eye drops, nasal drops and other commonly administered pharmaceutical compositions.

It is envisaged that special requirements for particular kits can be provided with variable concentrations of the active agents, zinc and trimethoprim from day to day to achieve the maximum effect without toxicity.

A variable or custom kit may be prepared to suit a particular clinical group or clinical setting.

A kit could optionally comprise different regimens, such as for example, covering the course day by day, with variable zinc concentrations, such as a high concentration in day 1 and reduced as the course progresses.

The kit may be in the form of a container accommodating a product comprising at least zinc and trimethoprim.

BRIEF DESCRIPTION OF THE DRAWINGS

The invention is illustrated by way of example only with reference to the following figures.

Figure 1:
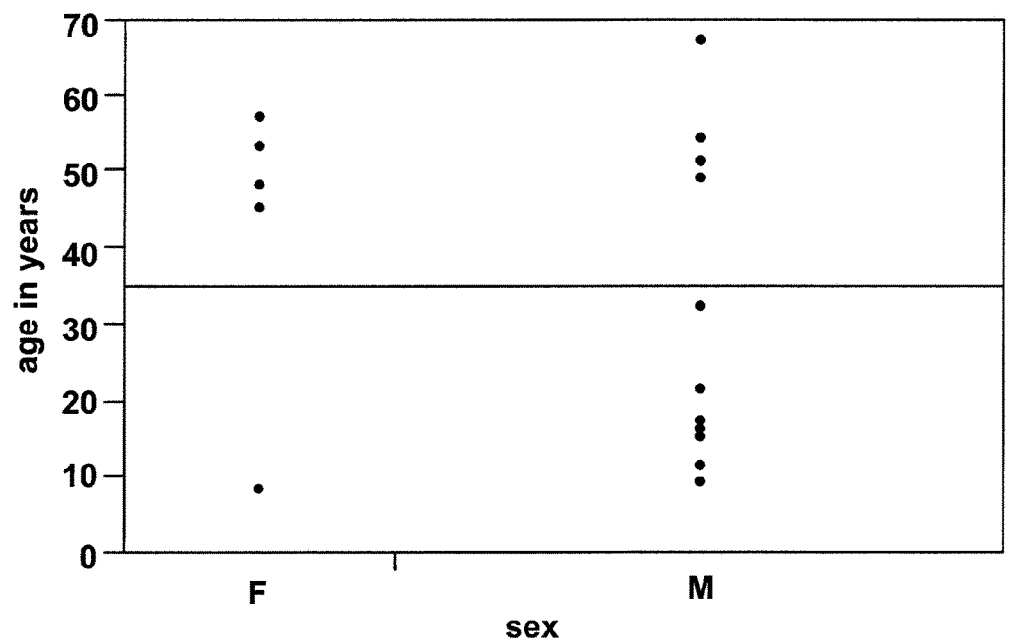
FIG. 1—shows the age and sex range of 16 patients in a viral respiratory infection study.

Trimethoprim (5-(3,4,5-trimethoxybenzyl)pyrimidine-2,4-diamine or $C_{14}H_{18}N_4O_3$) has the following chemical structure:

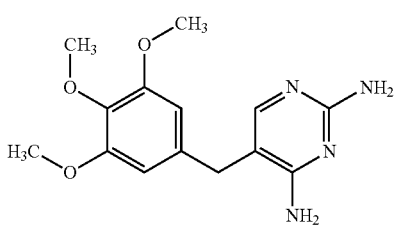 [SMILES: COc1cc(Cc2cnc(N)nc2N)cc(OC)c1OC]

DETAILED DESCRIPTION OF THE PREFERRED EMBODIMENT

Without the inventor being bound to any particular theory of interaction of zinc and trimethoprim in a subject suffering from a viral infection, the inventive composition is thought to act by preventing viral entry into the cell and by stopping its replication. Thus, further infection of cells is stopped and tissue recovery is then allowed to take place. It may be that the effect of the zinc and trimethoprim composition is achieved and/or enhanced by its simultaneous presentation to the cell and the virus.

Virus infection of cells requires adhesion to cell surface receptor and internalization. The binding requires glycoprotein whereas glycolipids are not essential to this process. Internalization of the virus contents uses clathrin and non-clathrin endocytosis. These processes are essential for viral infection. Once viral entry into the cell has occurred however, viral replication occurs in ribosomes. Alteration of the structure of the surface glycoprotein receptor prevents viral entry and infection of cells. Disruption of intracellular protein synthesis is another mode of combating the infective virus, by preventing or hampering its replication.

Without being bound to this theory alone, the inventor has proposed that providing an inhibitor of the replication process of the respiratory viruses (RNA viruses) would result in hampering viral replication, and that disturbing DNA function in a subclinical way by the inventive composition of zinc and trimethoprim would show such impact on the virus while not affecting the cell. This broad approach to prevent viral replication overcomes the potential of development of mutant strains that can be otherwise more difficult to treat.

The following schema shows the inventor's proposed mechanism of action of the antiviral composition of the invention to treat viral respiratory infection. The zinc and trimethoprim composition (shown in the figure as Tri-z) acts at several sites. The presence of the zinc/trimethoprim composition in the extracellular matrix blocks the virus from binding to the cell surface molecules thus prevents it from entry. If the virus succeeds in entering the cell, inhibition of protein synthesis that can be essential for viral replication would reduce its ability to replicate. The changes that the zinc/trimethoprim combination composition incurs of the cell membrane would also prevent the virus from exiting the cell. Thus, eradication of infection can occur in a short time.

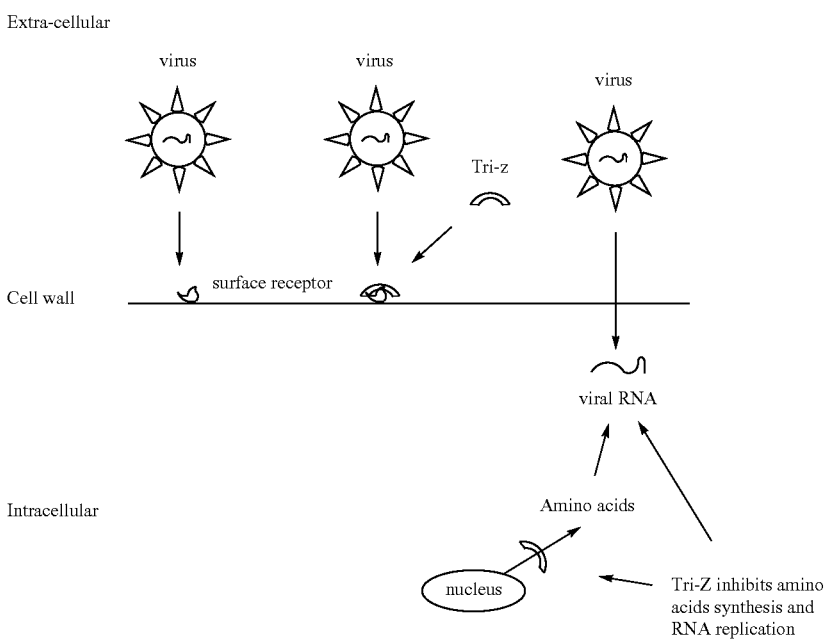

Trimethoprim has multiple potential binding sites for metal ions. X-ray crystallographic studies have been carried out to investigate metal complexes of trimethoprim, including zinc, cadmium and copper and have shown that such structures have antibacterial capability against a variety of bacterial strains (see B. Simó et al., 2000).

In the active zinc/trimethoprim compositions of the present invention, zinc and trimethoprim may combine to form a mixture in a variety of different ways. The inventive compositions are not bound to any one structure in particular.

For example, zinc may either be (i) chemically bonded to trimethoprim as shown in the structure of the zinc/trimethoprim complex [Zn (trimethoprim)$_2$Cl$_2$] obtained from x-ray crystallographic data as a ZORTEP plot (see L. Zoslnai, ZORTEP. A program for the Presentation of Thermal Ellipsoids, University of Heidelberg, Germany, 1997) of the structure of a zinc/trimethoprim mixture:

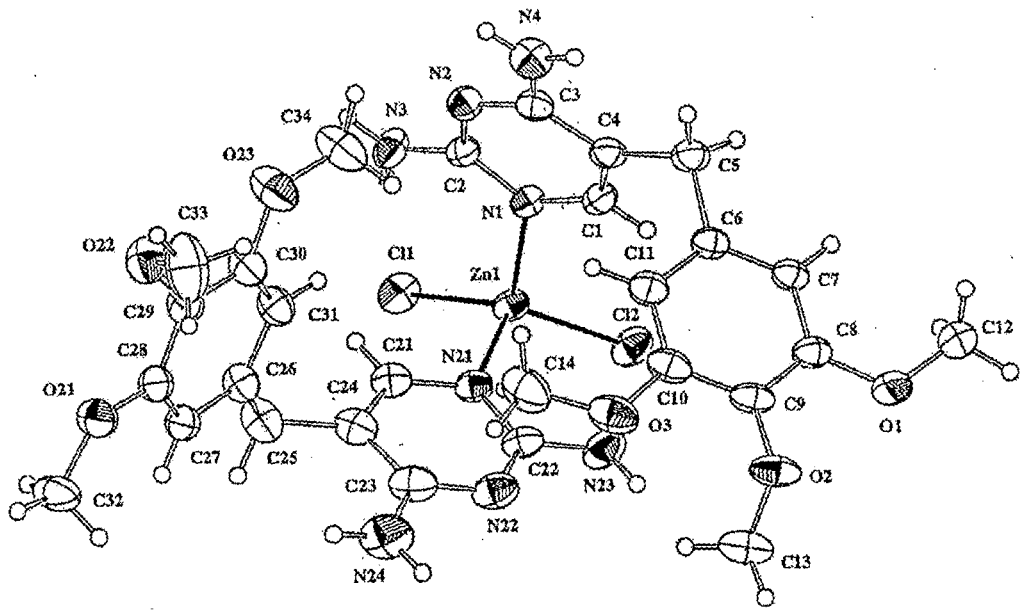

or (ii) may be present within the folds of the trimethoprim molecule. The putative structure shown above is representative of such zinc/trimethoprim complexes as are used in the instant inventive approach.

Structures 1 to 14 shown in Table 1 below, exemplify alternative stereochemical representations of how the zinc and trimethoprim may be combined in the active zinc/trimethoprim compositions of the present invention, in which R indicates the possible positions of zinc.

Table 1

Structure 1

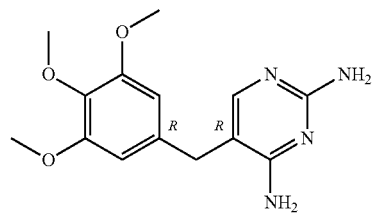

Structure 2

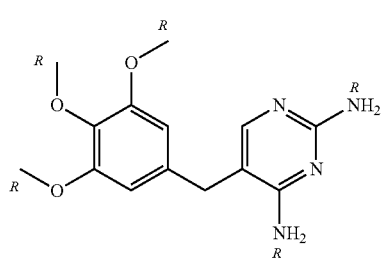

-continued

Structure 3

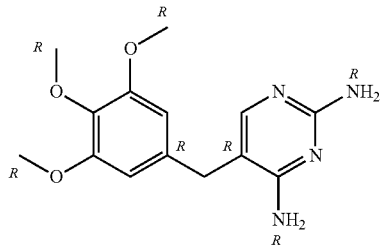

Structure 4

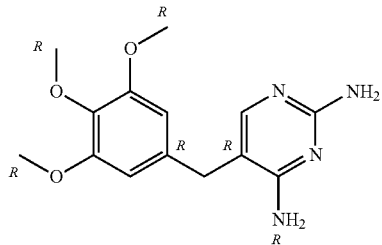

Structure 5

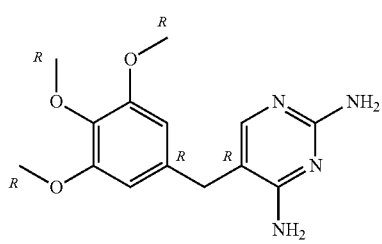

-continued

Structure 6
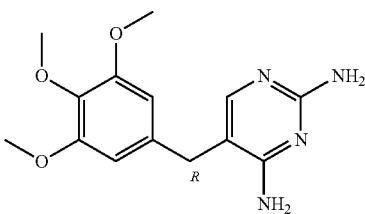

Structure 7
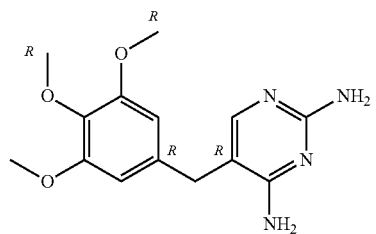

Structure 12
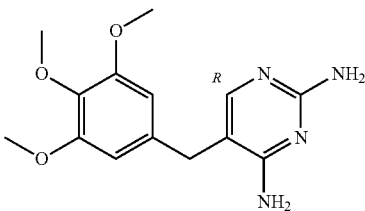

Structure 8
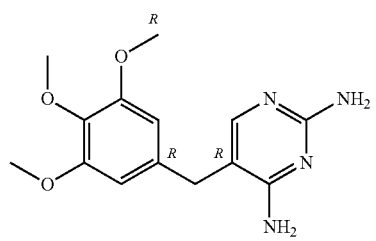

Structure 13
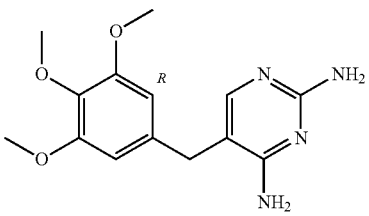

Structure 9
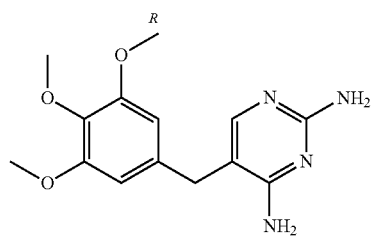

Structure 14
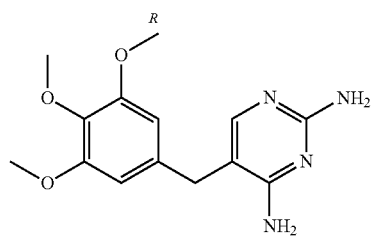

Structure 10
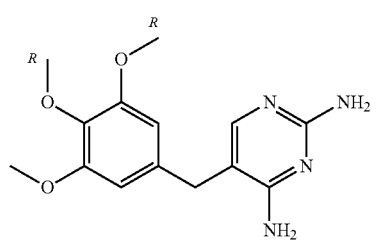

Structure 11
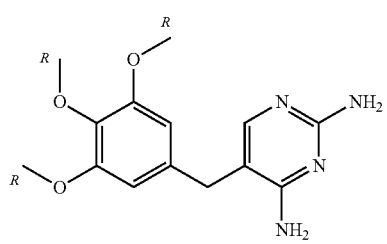

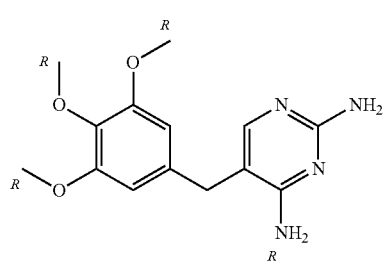

There are several ways a zinc moiety can form an association with a trimethoprim moiety as contemplated in the present invention and the inventor is not bound by any particular chemical association of the zinc moiety and the trimethoprim moiety.

Figure 9A:
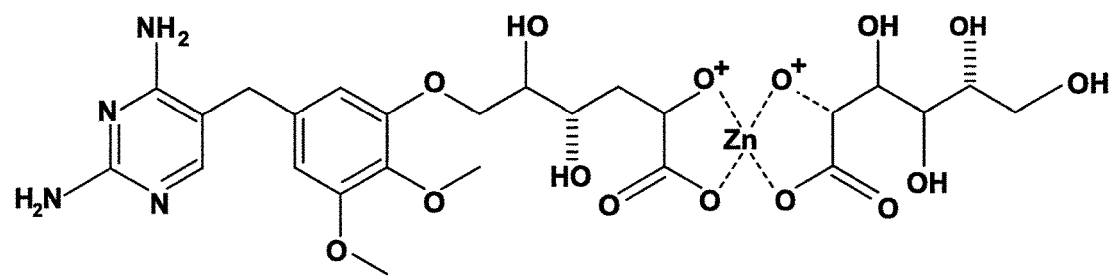
FIG. 9 (*a*)-(*g*)—shows exemplary zinc-trimethoprim complexes for use in the inventive compositions.
Figure 9B:
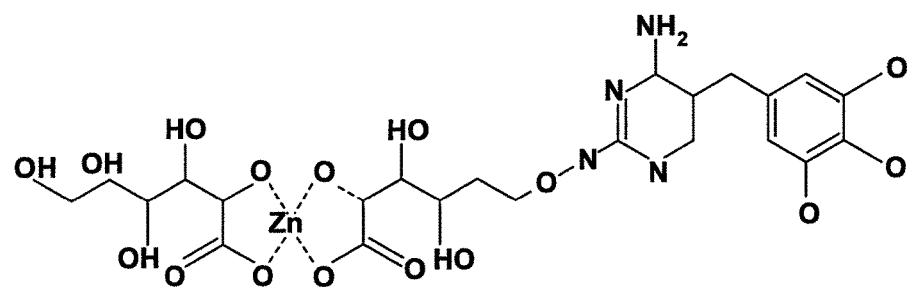
Figure 9C:
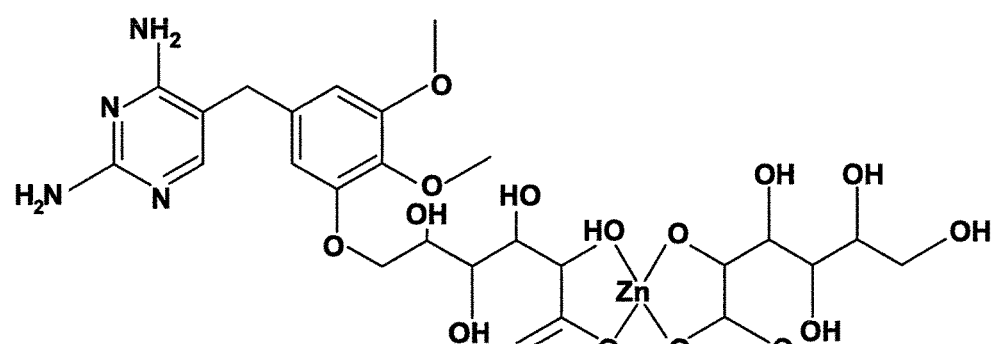
Figure 9D:
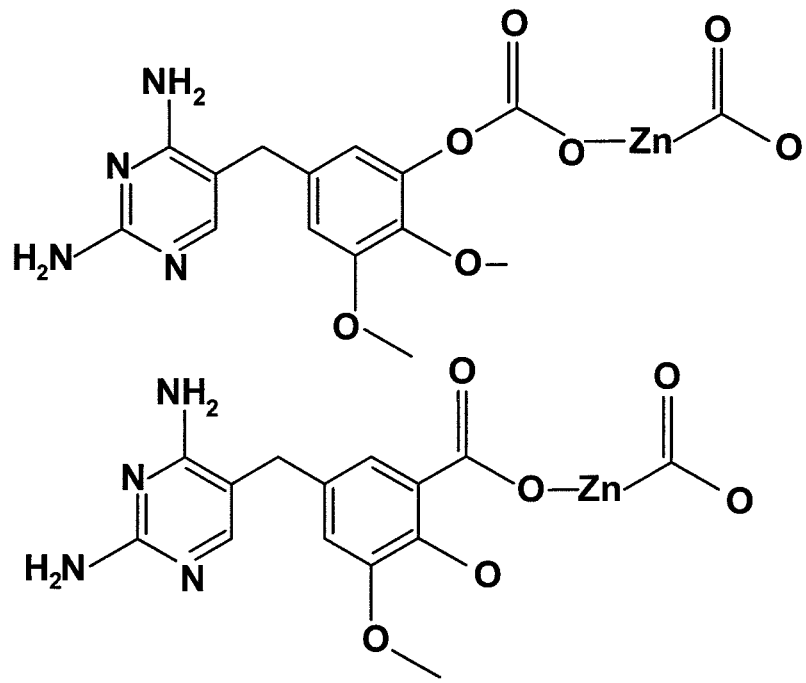
Figure 9E:
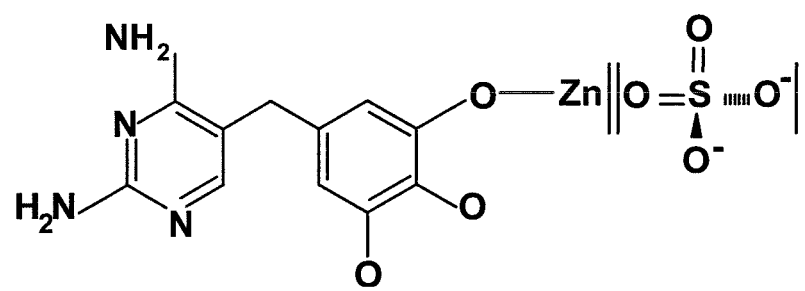
Figure 9F:
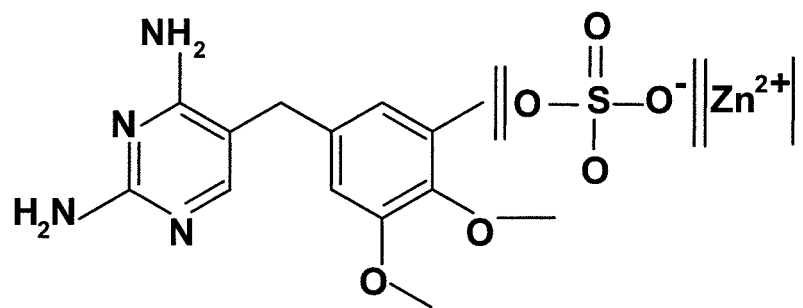
Figure 9G:
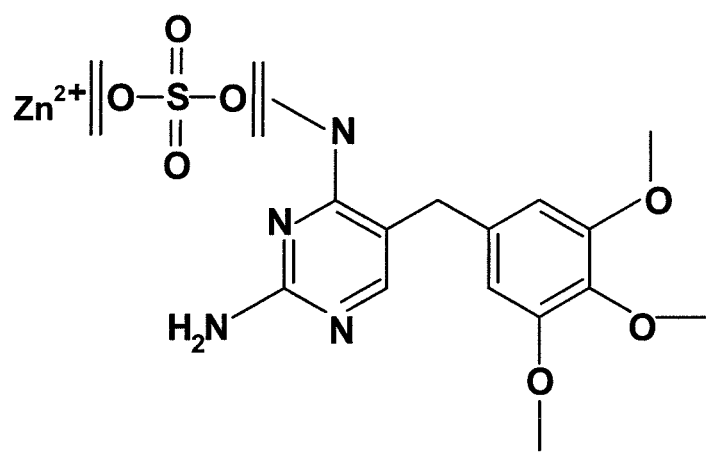

For example, zinc gluconate, zinc acetate and zinc sulphate may be combined with trimethoprim with effect as contemplated in the present invention. FIG. 9 (a)-(f) show exemplary zinc-trimethoprim complexes for use in the inventive compositions. FIG. 9 (a) shows an exemplary zinc gluconate-trimethoprim complex that may be administered to a subject in need. FIG. 9(b) shows a different zinc glucomate-trimethoprim complex. Although zinc gluconate (zincum gluconium) is an ionic compound being the zinc salt of gluconic acid, having two moles of gluconate for each mole of zinc, in the compositions described herein, the zinc moiety may be associated with the trimethoprim moiety in other forms of an association between a zinc gluconate and trimethoprim molecules, not necessary ionicly bonded—the doted line in FIG. 9(b) shows how the two compounds may be associated rather than bonded together. FIG. 9(c) shows a third type of zinc glucomate-trimethoprim complex. Other forms of association of the zinc glucomate and the trimethoprim molecule in a complex are also contemplated in the claimed invention. FIG. 9(d) shows two different exemplary zinc acetate-trimethoprim complex structures. Other forms of association of the zinc acetate and the trimethoprim molecule in a complex are also contemplated in the claimed invention. FIG. 9(d) shows two exemplary zinc sulphate-trimethoprim complexes, which are representative but do not exclude a complex comprising other forms of an association of a zinc sulphate molecule and a trimethoprim molecule. FIGS. 9 (e)-(g) show three alternative exemplary complexes formed between zinc sulphate and trimethoprim, although other forms of association between zinc sulphate and trimethoprim are contemplated in the invention.

EXAMPLES

Example 1

Two groups of patients having viral infection, Group A and Group B, were treated with zinc/trimethoprim compositions.

Viral Infection

In addition to the clinical presentation, diagnosis of viral infection in each of the patients was confirmed by IFA (immunofluorescence assay) showing viral presence in a clinical sample such as in a nasal aspirate, for example, influenza A or B. IFA permits rapid detection of viral infection to permit early treatment and eliminate delay and can be carried out on simple clinical samples such as an aspirate but does not distinguish subtypes. RT-PCR (reverse transcriptase-PCR) was used for subtyping and for detection of rhinovirus. RT-PCR is done on swabs. In the case of the patient groups, RT-PCR determined the presence of subtypes influenza H3, rhino virus and RSV. IFA and RT-PCR was repeated after treatment to ensure viral eradication from the patient.

Example 2

Group A Patients—Clinical Findings

Figure 2:
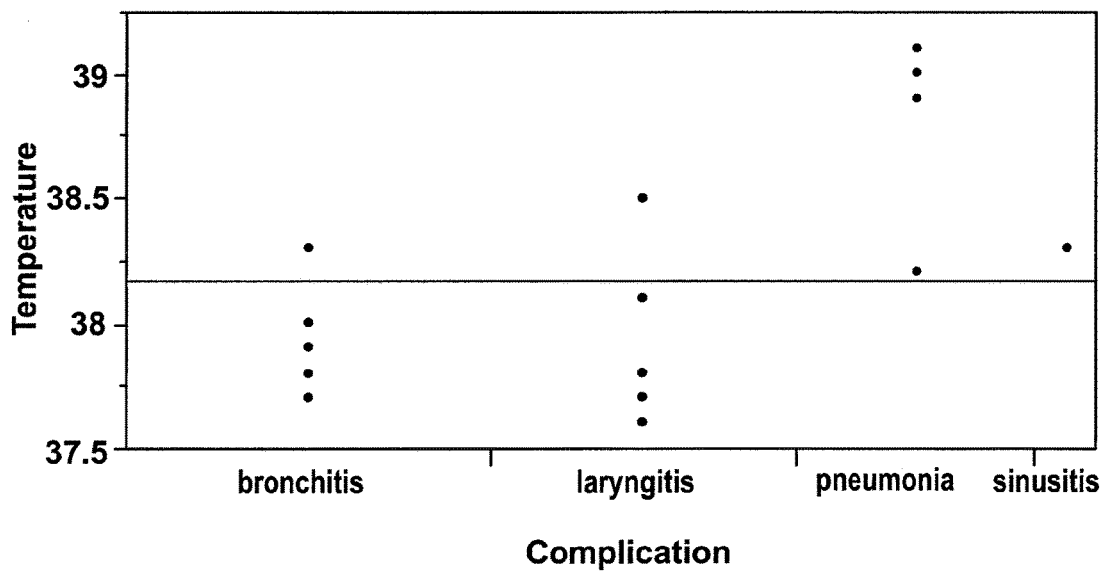
FIG. 2—shows the range of influenza complications in the 16 patients in a viral respiratory infection studied.

Group A patients included 16 patients, aged 11 to 67 years, 11 men and 5 women, with proven viral respiratory infection. The 16 patients who presented on day 10-18 of illness with severe complicated influenza were examined and it was found that there were four pneumonia subjects (n=4), six bronchitis subjects (n=6), five laryngitis subjects (n=5), and one sinusitis subject (n=1). FIG. 1 shows the age and sex of these 16 patients. FIG. 2 shows the range of severe complicated acute influenza in the 16 patients. Diagnosis was confirmed by laboratory testing for the type of infection in nose and throat swabs and nasal aspirate. The viruses were 1) influenza A/H3 (number of subjects, n=11); Influenza B (n=5); Rhino virus (n=2); and RSV (n=2).

A trimethoprim and zinc sulfate mixture was administered to all 16 subjects. They all reported recovery full to partial within 48 hours.

Dosage

The zinc/trimethoprim compositions (Tri-Z) administered were in the following dosage range: 0.18 mg of zinc to 1 mg of Trimethoprim for dosages of 100 mg (82 mg Trimethoprim and 18 mg Zinc) to dosages of 400 mg (328 mg Trimethoprim and 72 mg zinc) once or twice daily for up to 5 days.

Figure 3:
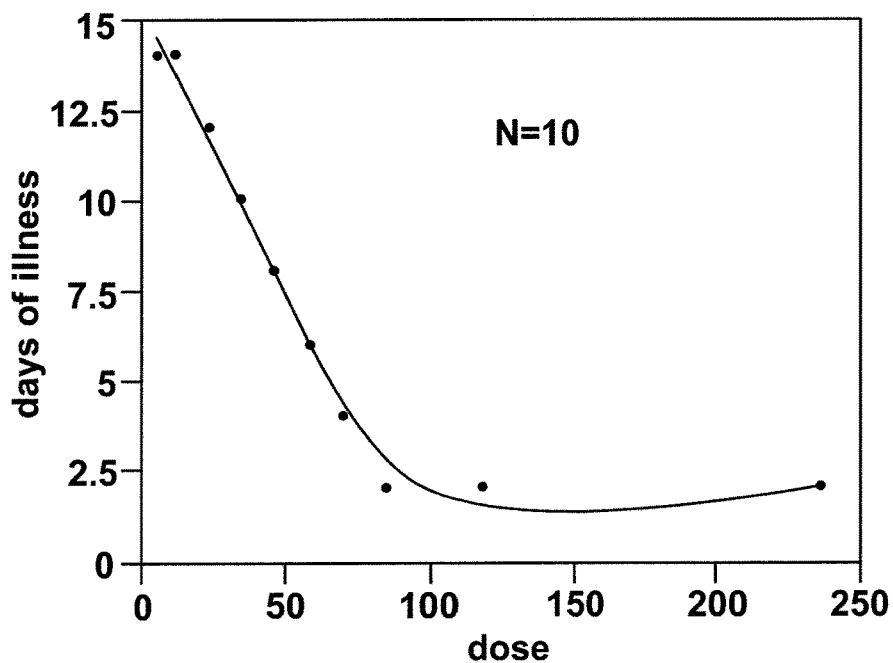
FIG. 3—shows a dose response curve for the zinc and trimethoprim composition (Tri-Z).

FIG. 3 shows the relationship between the dose of a zinc and trimethoprim mixture and the duration (in days) of illness. In FIG. 3, the dose (mg) response curve shows the effects of the administration of Tri-Z up to 10 doses (n=10) at increasing dosage, when the duration of illness was monitored.

In severe infection, an initial dose of 400 mg was administered followed by 200 mg doses twice daily for up to 4 days. Increasing doses of combined trimethoprim/zinc at the suggested concentration ratio, was administered to 10 subjects with uncomplicated influenza to evaluate its effect on duration of illness. In contrast to length of time taken to successfully treat uncomplicated influenza, usually 7 to 14 days, and the mixture was effective in reducing the duration of the illness to only 2 days at a dose of 80 to 100 mgs in an average size adult (60 kg), twice daily.

Exemplary Clinical Findings (i) 11 year-old male, presented with fever, headache, body ache, cough, runny and blocked nose for 11 days. He had persistent cough for the last week that is getting more frequent and in attacks that made him faint on one occasion. Temperature 37.8, good air entry, respiratory rate 20/min, heart rate 86/min. Nasal aspirate was taken using a suction catheter and nasal swab.

He returned for review 3 days later for review. His symptoms were unchanged, cough was same and temperature was 38 C. Throat swab was taken for culture and sensitivity and RT-PCR. Nasal swab was taken for virus identification using IFA (immune-florescence assay). The results of the laboratory showed influenza virus type B and no bacterial growth. He was prescribed trimethoprim 100 mg and zinc sulphate 5 mg both to be taken simultaneously twice daily on an empty stock at least 1 hour before meal. One tablet of zinc sulphate dissolved in 9 mls water and take one ml and add to it a trimethoprim tablet and be taken as one medicine.

He returned for another review 2 days latter, his temperature was 36.8 C, cough has stopped, no other symptoms except snuffle. Nasal aspirate was taken for IFA and was negative for virus. He stopped treatment after 3 days. He was reviewed again at 5 days from starting treatment he was back to normal and back to school.

(ii) 15 year-old male presented with headache, body ache, cough, runny blocked nose, watery eyes, getting short of breath for the last 16 days. He was given Amoxicillin for 5 days between day 4 and day 9 of the illness without any effect. Temperature 39 C. Respiratory rate 30/min. Clinical examination suspected right middle lobe pneumonia.

Chest Xray confirmed diagnosis. Nasal aspirate and throat swabs were taken for bacterial and viral detection. IFA showed influenza type A/H3. Bacterial cultures were negative. Full blood count showed white cell $6 \times 10^9/1$, neutrophil of $3 \times 10^9/1$, lymphocytes $3 \times 10^9/1$. Blood culture were negative for bacterial infection. C-reactive protein was 1.

He was started on trimethoprim 200 mg and 45 mg zinc sulphate (both mixed in the same cup and taken simultaneously on an empty stomach)

He was reviewed on day 2 of treatment and he was well, temperature was 37 C, respiratory rate was 20/min. He continued of treatment and on day five he was fully active, apyrexial, nasal aspirate was examined by IFA and was negative for virus. The white cell count after treatment on day 5 was $8 \times 10^9/1$ with neutrophils count at $6 \times 10^9/1$, lymphocyte count was $3 \times 10^9/1$, and basophils were $0.5 \times 10^9/1$. Thus, the neutrophil count was restored to a normal level. C-reactive protein remained at 1.

Treatment was stopped and patient returned to school.

Example 3

Temperature Studies

Figure 4:
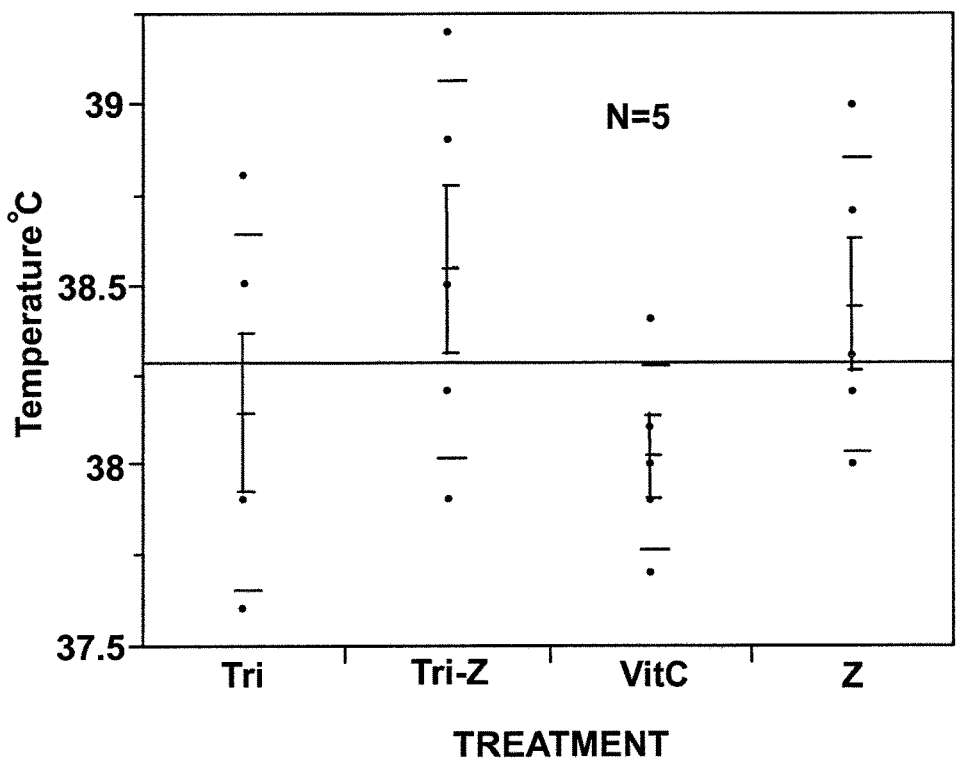
FIG. 4—graph showing the variation of temperature with treatment regimes comparing the zinc and trimethoprim composition (Tri-Z) with zinc alone, trimethoprim alone or vitamin C alone, in treating viral upper respiratory tract infections.

In another study, four separate groups of patients were studied in which temperature was a marker of illness severity so that the effect of temperature during illness upon recovery rate could be determined. FIG. 4 shows temperature of the four groups in which each group received a different treatment regimens, showing that for the four groups of patients each receiving a different treatment admixture (one group receiving trimethoprim alone, one group receiving zinc alone, one group receiving Vitamin C alone and a fourth group receiving a mixture of zinc and trimethoprim), there was no significant difference in temperature between the four groups of subjects and indicating that the temperature exhibited by the patient did not signify as a reason for the difference in recovery rate upon treatment.

Example 4

Clinical Findings—Group B Patients

Group B patients included 20 patients, aged 19 years to 57 years, 14 men and 6 women, with influenza but uncomplicated upper airway infection. Nasal aspirate and swabs showed viral but no bacterial growth. The viruses identified were Influenza A, B and Rhino virus.

On day 3-5 of the illness (influenza) they received either a zinc/trimethoprim mixture, zinc, trimethoprim alone or vitamin C alone in a randomized double blind trial. The subjects were reviewed at 2 and 5 days after starting treatment. Those who received the zinc/trimethoprim mixture showed recovery from 2 days after treatment and back to normal by day 5, whereas those with other modes of treatment were still feeling off and not back to normal.

Dosage

With complicated cases as shown in Group B, a higher dose of the mixture was administered of 200 mg or above twice a day.

The Tri-Z dose ranged between 100 mg (82 mg Tri and 18 mg zinc) to 200 mg (164 mg Tri and 36 mg zinc) twice daily. Trimethoprim only was administered in quantities of between 100 mg and 200 mg twice daily. Zinc only was administered in quantities of 50 mg three times daily. Vitamin C was administered in 1 g quantities twice daily.

Figure 5:
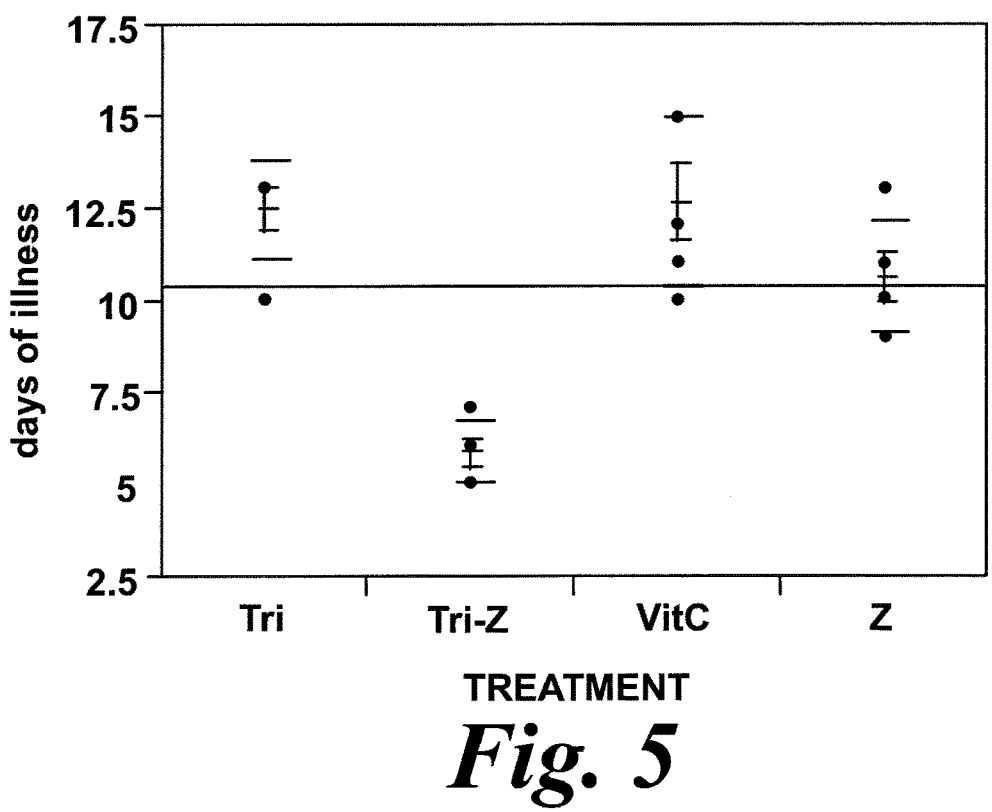
FIG. 5—graph showing the days of illness versus the treatment regime.
Figure 6:
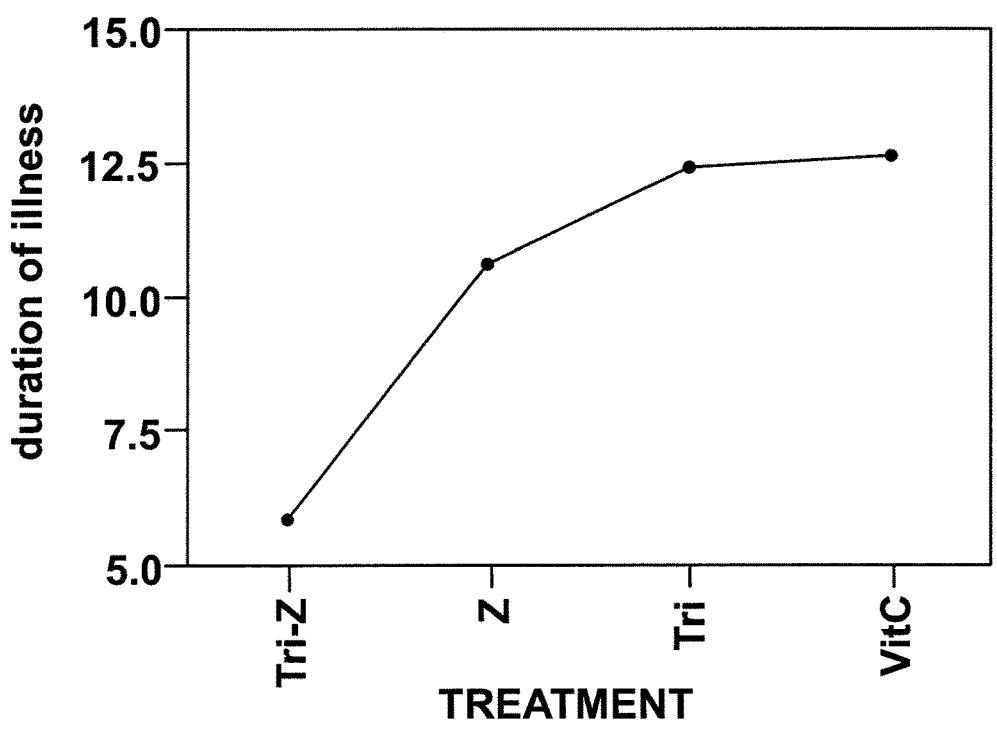
FIG. 6—shows duration of viral infection illness with respect to treatment regime.

FIGS. 5 and 6 illustrate that for the 20 patients (19-57 years of age) presenting with uncomplicated viral upper respiratory tract infections (URTI), Tri-Z causes a marked reduction in the total duration of illness in five subjects treated with Tri-Z compared to other groups of five subjects receiving treatments of zinc or zinc compounds alone, trimethoprim alone, and vitamin C alone.

Points on the graph shown in FIG. 6 are group means (for n=5) which highlights the difference in illness duration. Patients who received Tri-Z showed recovery starting 2 days after treatment commenced and were back to normal by day 5. Repeat IFA and RT-PCR tests were negative by day 2. Patients having one of the other three modes of treatment were still feeling unwell and not back to normal at day 5, and repeat IFA and RT-PCR tests were positive at day 2.

Figure 7:
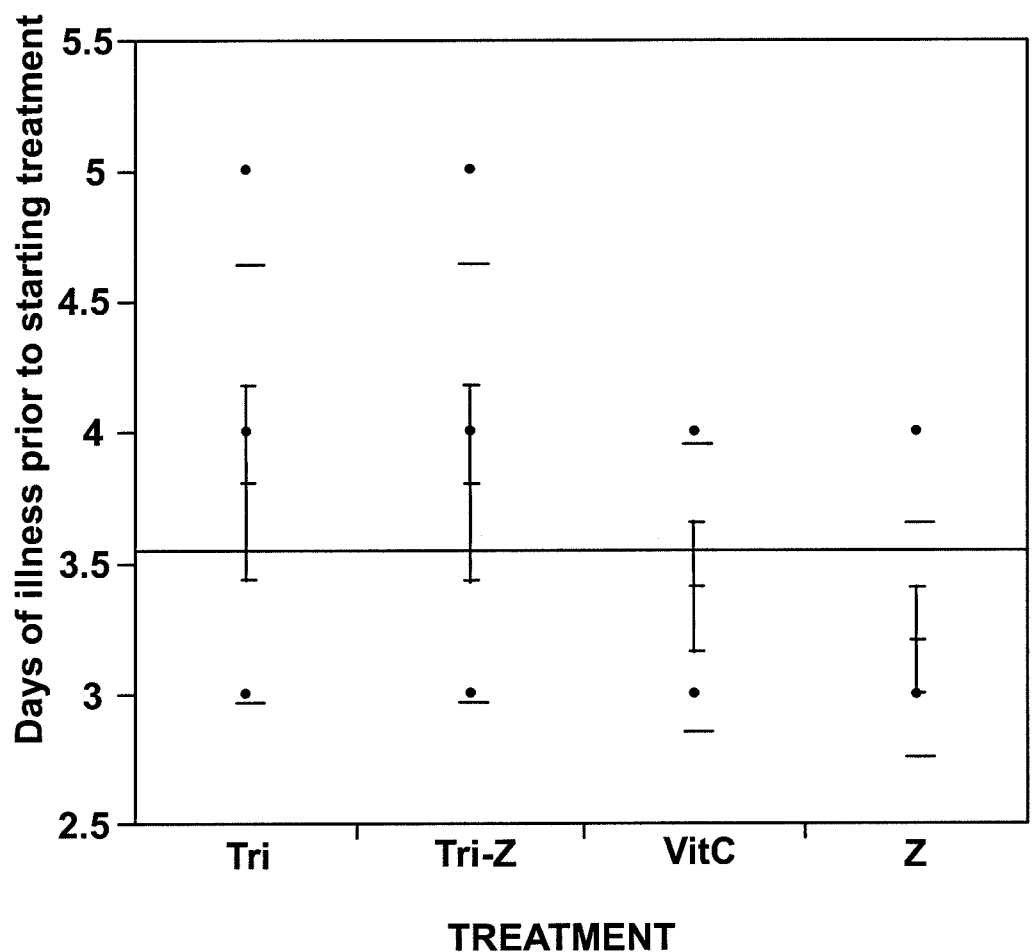
FIG. 7—shows days of illness prior to starting treatment with different treatment regimes.
Figure 8:
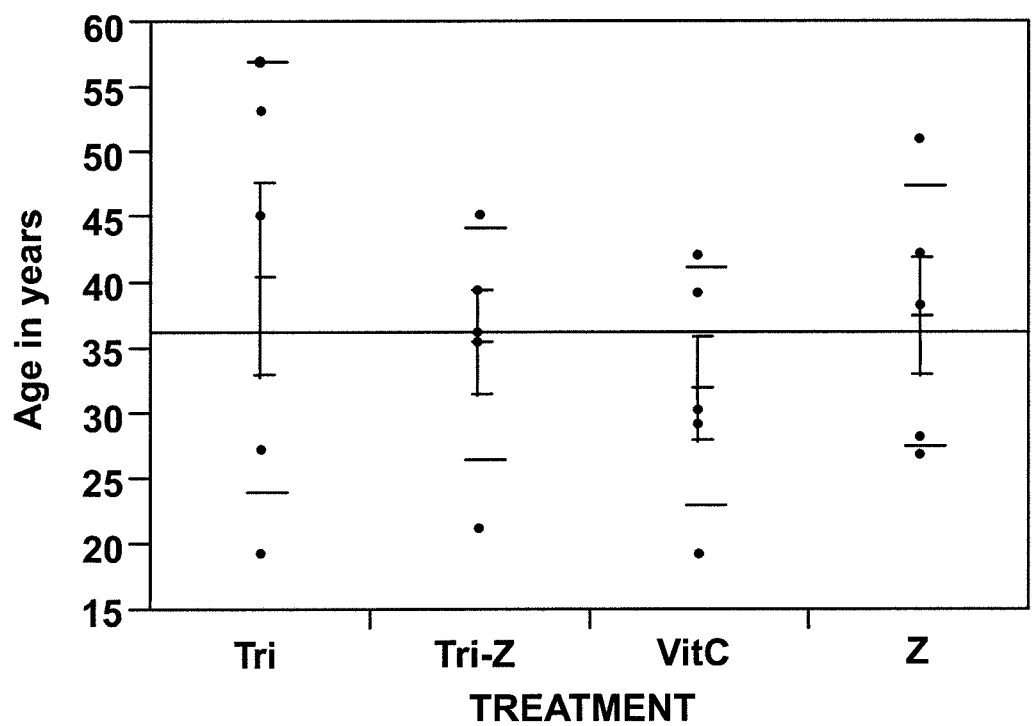
FIG. 8—shows age variation with respect to treatment regime.

FIG. 7 shows that there was no significant difference of the duration of illness in days between the groups (n=5, p<0.2) prior to starting treatment. FIG. 8 demonstrates that age distribution was similar between groups (n=5, p<0.2).

Exemplary Clinical Findings (i) 45 year-old man presented with headache, no photophobia, body ache, feeling tired and lethargic, blocked runny nose, dry throat and feeling hot for the last 4 days. Temperature was 38.5 C, respiratory rate 18/min, heart rate 75/min regular, BP 115/70 mmHg, clear nasal discharge, blood shot eyes, clear throat. Chest was clear with normal breath sounds. No cervical lymph nodes.

Nasal aspirate and throat swab was taken for virus and bacteria. IFA and RT-PCR showed influenza type A/H3 (next day results). Cultures were negative for bacterial growth at 48 and 72 hours.

He was commenced on the zinc/trimethoprim mixture twice daily (initial dose 200 mg of trimethoprim and 100 mg zinc sulphate for first dose then reduced to 100 mg of trimethoprim and 50 mg of zinc sulphate given simultaneously on an empty stomach) for 5 days.

On day 2 of treatment he was reviewed. He was well, temperature 36.9 C, heart rate and respiratory rate were normal and he was asymptomatic. Nasal aspirate was taken and IFA was carried out and did not show any virus. Treatment was stopped on day 3. He was contacted on day 5 and he was at work and back to normal.

(ii) 51 year old man presented with body ache, generally feeling tired, blocked runny nose, sore eyes, dry throat, headache and feeling hot for the last 4 days. His temperature was 38 C. His chest was clear with normal breath sounds. Respiratory rate 16/min, heart rate 84/min regular, BP 135/78 mmhg. Nasal aspirate and throat swabs was taken for virus and bacteria.

Same day results showed influenza type B. He was started on zinc sulphate 100 mg twice daily. Bacterial culture at 48 and 72 hours were negative.

He was reviewed 2 days after treatment he was the same feeling and getting cough. Repeat viral test showed influenza type B.

He was reviewed on day 5 after treatment his cough reduced, headache is still occurring controlled by paracetamol, stiff blocked nose and dry throat and general body ache still present. He stopped taking treatment as it was ineffective in controlling his symptoms. Further sample of nasal aspirate was taken and it showed influenza type B. He returned to work on day 14 of the illness with still h=feeling unwell, body ache and blocked nose.

(iii) 27 year-old male presented with feeling hot, blocked nose that is runny, headache, body ache, dry cough, sore eyes for last 4 days.

Temperature was 38.5 C, heart rate 60/min, respiratory rate 16/min, BP 120/70 mmHg, chest clear with normal breath sounds, no lymphadenopathy, conjunctival congestion, throat clear.

Nasal aspirate and throat swab were taken for virus and bacteria. He was started on Trimethoprim 200 mg twice daily for 5 days. IFA showed influenza type B. Bacterial cultures were negative at 48 and 72 hours.

He was seen 2 days later and he was the same. He was reviewed on day 5 of treatment. His temperature was 37.8 C, still headache and sore eyes and blocked nose. Nasal aspirate and culture were taken. It showed influenza type B and no bacterial growth. Treatment was stopped. He started to recover on day 14 of the illness when he felt well enough to go back to work.

What is claimed is:

1. A pharmaceutical composition for treating a viral infection in a subject in need thereof, the composition comprising an effective amount of zinc, trimethoprim, and a pharmaceutically acceptable carrier or diluent, wherein the weight ratio of zinc to trimethoprim in the composition is from 1:3 to 1:7, and wherein the zinc is in an amount of 0.1 to 22.5 mg and the trimethoprim is in an amount of 1 to 200 mg.

2. The composition of claim 1, further comprising one or more of: an adjuvant, an excipient, a buffer, a matrix, a binder, a coating material, an analgesic, a vitamin, a sweetener, a flavour, a sustained release vehicle and an additional therapeutic agent.

3. The composition of claim 1, wherein the composition is formulated as a prolonged release medication, an injectible fluid, an aerosol, a gel, a pill, a capsule, a lozenge, a gargle, a nasal drop, an eye drop, a syrup, a dissolvable tablet, an enterically coated tablet, a dermal application or a transdermal patch.

4. The composition of claim 1, wherein the composition comprises a pharmaceutically acceptable salt of any one or more of: zinc, trimethoprim, and an admixture of zinc and trimethoprim.

5. The composition of claim 4, wherein the salt is one or more of: $C_{14}H_{18}N_4O_3 \cdot ZnSO_4$, $C_{14}H_{18}N_4O_3ZnC_4H_6O_4$, and $C_{14}H_{18}N_4O_3 \cdot ZnO_{14}H_{22}C_{12}$.

6. The composition of claim 4, wherein the zinc salt is one or more of: zinc sulphate, zinc acetate and zinc gluconate.

7. The composition of claim 1, wherein the composition comprises a zinc and trimethoprim complex.

8. A pharmaceutical composition for treating a viral infection in a subject in need thereof, the composition comprising an effective amount of zinc, trimethoprim, and a pharmaceutically acceptable carrier or diluent, wherein the weight ratio of zinc to trimethoprim in the composition is from 1:3 to 1:7, and wherein the zinc is in an amount of 50 to 250 mg and the trimethoprim is in an amount of 500 to 1000 mg.

9. The composition of claim 1, comprising one or more of Structures 1-14:

Structure 1

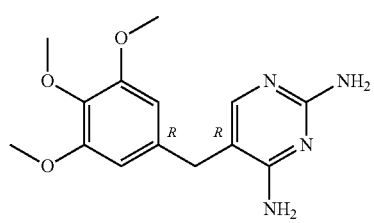

Structure 2

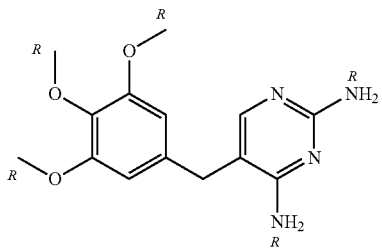

Structure 3

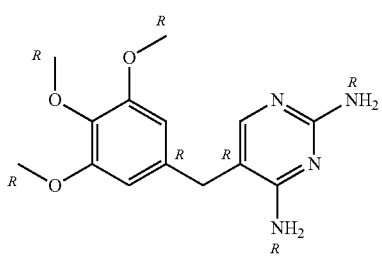

Structure 4

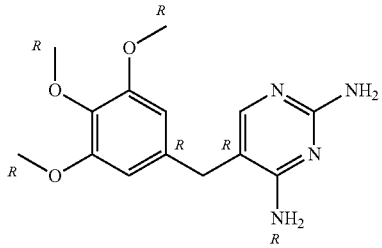

-continued

Structure 5

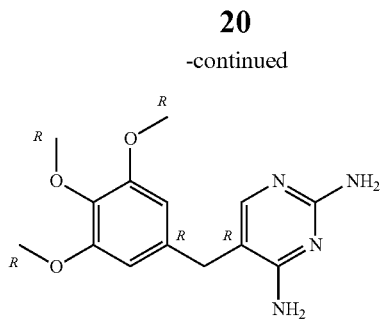

Structure 6

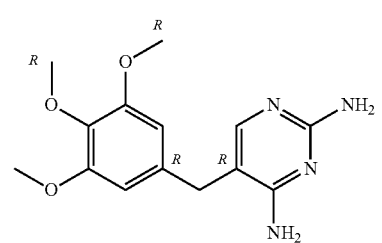

Structure 7

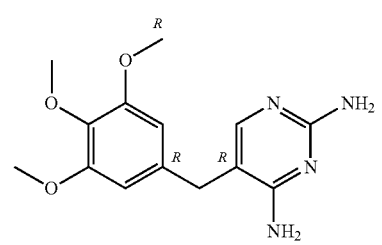

Structure 8

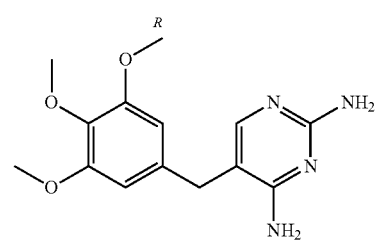

Structure 9

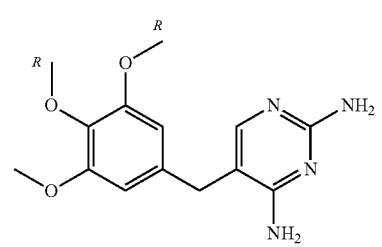

Structure 10

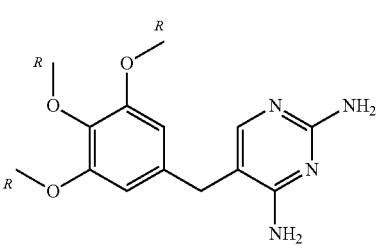

Structure 11
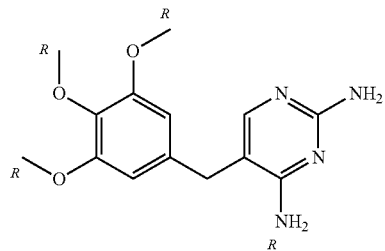
Structure 12
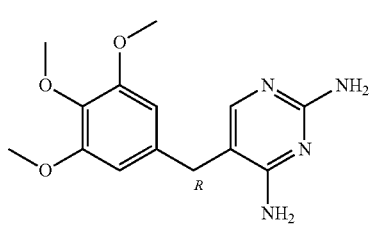
Structure 13
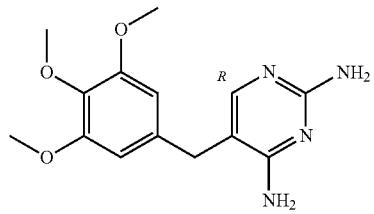
Structure 14
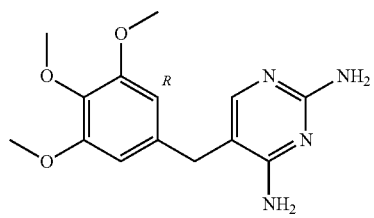
wherein possible positions of the zinc are indicated by R.
* * * * *